United States Patent [19]

Smith et al.

[11] Patent Number: 5,078,954
[45] Date of Patent: Jan. 7, 1992

[54] METHOD AND APPARATUS FOR CARRYING OUT THE IN SITU INSPECTION OF THE SHAFTS OF PUMPS

[76] Inventors: Thurman D. Smith, 407 Avenida Arboles, 95123; James C. S. Tung, 1244 Whitehall Ave., both of San Jose, Calif. 95128; James H. Oates, 9420 Burchell Rd., Gilroy, Calif. 95020

[21] Appl. No.: 511,119

[22] Filed: Apr. 17, 1990

[51] Int. Cl.$^5$ .............................................. G21C 17/00
[52] U.S. Cl. .................................... 376/245; 376/260; 73/623
[58] Field of Search ............... 376/245, 252, 249, 260; 73/623

[56] References Cited

U.S. PATENT DOCUMENTS

| | | | |
|---|---|---|---|
| 3,810,384 | 5/1974 | Evans | 73/67.8 S |
| 3,961,523 | 6/1976 | Cornforth | 73/67.8 S |
| 4,394,345 | 7/1983 | De Briere et al. | 376/245 |
| 4,597,294 | 7/1986 | Brill, III et al. | 73/623 |
| 4,899,590 | 2/1990 | Light et al. | 73/622 |

Primary Examiner—Brooks H. Hunt
Assistant Examiner—Chrisman D. Carroll

[57] ABSTRACT

Method and apparatus for carrying out the in situ inspection of the shaft of a pump. A spacer coupling or link is manually removed from a limited access area intermediate the pump drive and top of the pump shaft. Inspection then is carried out through a previously formed inspection bore extending concentrically along the interior of the shaft. A probe supported by an extension assembly is lowered into the inspection bore until characterizable portions of the shaft such as a labyrinth seal region are identified. A discrete small region of interest which will initially evidence any fault condition then is surveyed with a raster scan movement of the inspection probe. Lower components of the region of interest are also identified by a next adjacent characterizable region such as a fillet welding for a journal assembly. Because of the limited longitudinal extent of the region of interest, the raster type movement of the probe becomes available. A calibration mock-up of the shaft is employed to provide ultrasonic signal readout information to apprise the operator of the presence of characterizable regions and the effectiveness of inspection transducer operation.

16 Claims, 9 Drawing Sheets

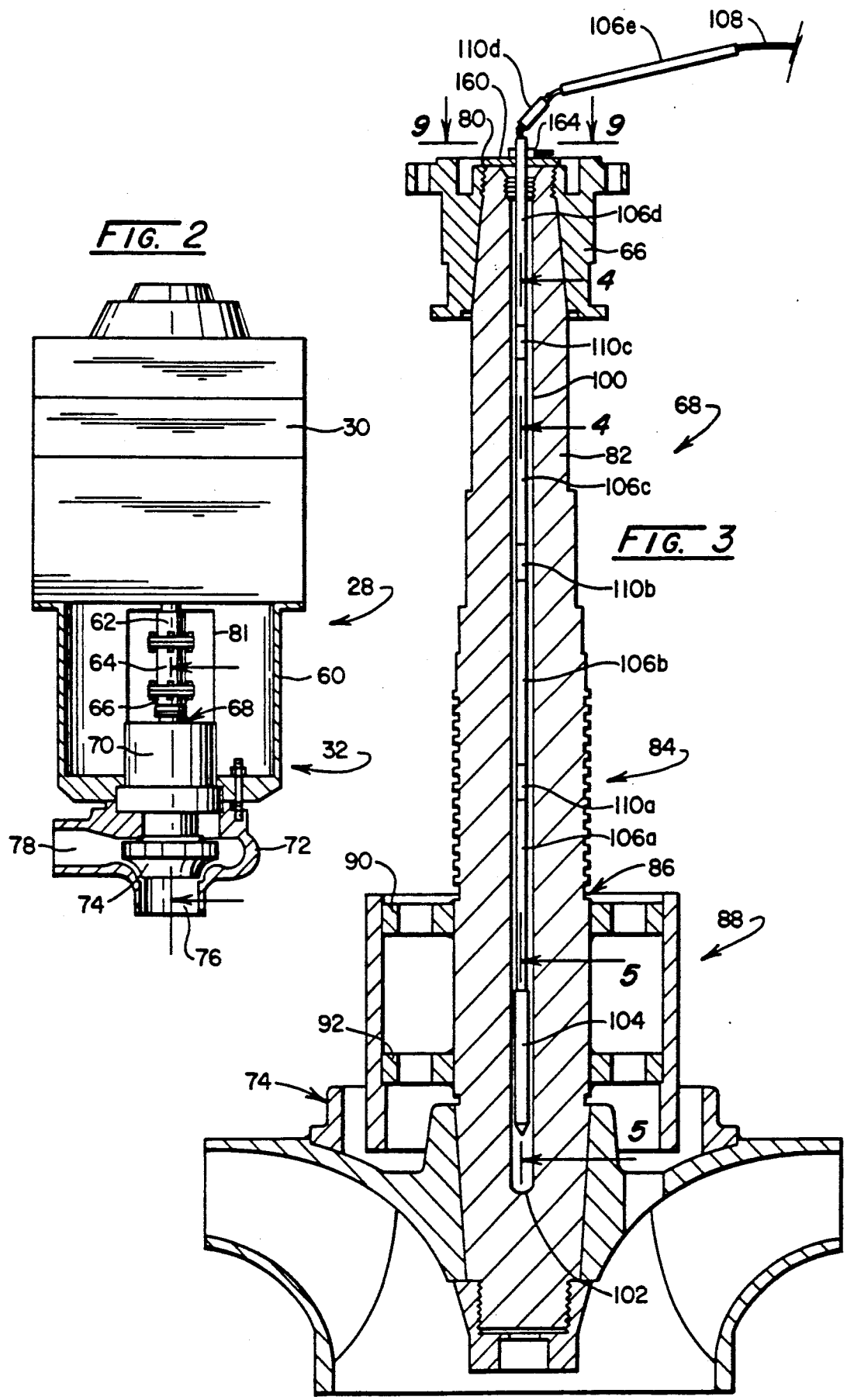

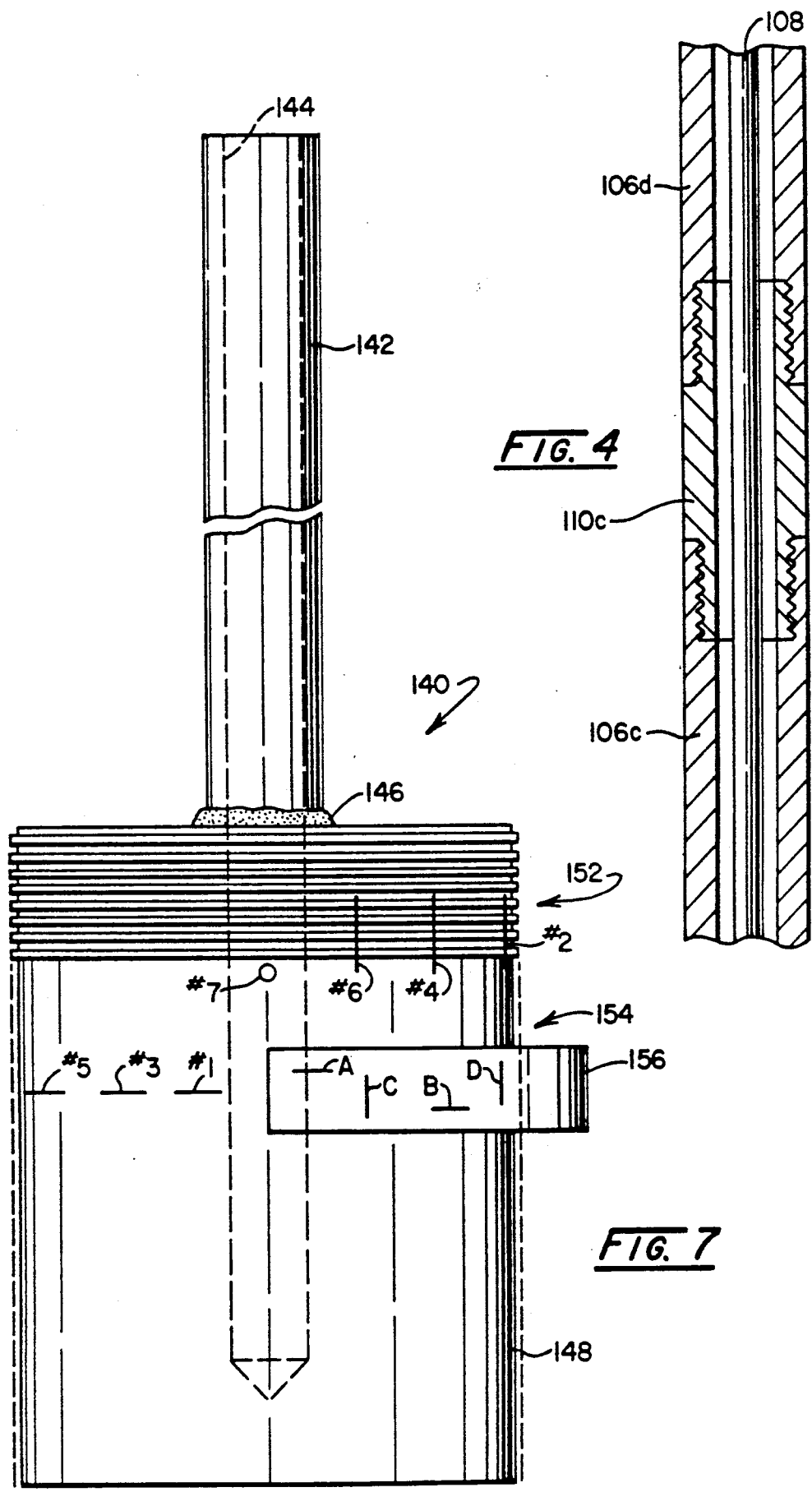

METHOD AND APPARATUS FOR CARRYING OUT THE IN SITU INSPECTION OF THE SHAFTS OF PUMPS

BACKGROUND OF THE INVENTION

In certain industries, pumps are used to circulate fluid that may contain potentially harmful or hazardous substances. Nuclear reactor and chemical installations are general examples of facilities that circulate such fluids.

Nuclear reactor installations circulate fluids that serve as moderators or coolant as well as working fluid that drives a turbine. In the discussion to follow, the use of such fluids is described in conjunction with a boiling water reactor form of nuclear power installation. Boiling water reactors (BWRs) are designed such that water, the primary coolant, serves both as a moderator and as a working fluid driving a turbine or the like. Thus, a single coolant loop is involved with these installations and the utilization of separate steam generators and the like is eliminated. Because of the boiling activity in the BWR core, such reactors are operated at advantageously lower system pressures than, for example, pressurized water reactors (PWRs). However, since the working fluid (water) passes through the reactor core in this direct cycle and out of the containment structure to drive a turbine or the like, particular care is paid to the avoidance of radiation hazards. While the primary water coolant is highly purified in such reactors to prevent activation of impurities when subjected to the high neutron fluxes extant in the core, induced radioactivity is witnessed in the circulating coolant. Thus, maintenance activities for BWR installations necessarily become more rigorous in order to account for these radioactive conditions.

In more typical BWR installations, water coolant is heated in the reactor core to rise within the reactor vessel as a two-phase mixture of water and steam. This dual phase mixture then passes upwardly through a steam separator assembly and steam dryer structure to enter a steam line leading to the turbine. Following turbine drive, the steam is condensed to water and returned to the reactor by quite large condensate and feedwater pumps. Generally large vertically oriented recirculation pumps are used to circulate the water through the reactor core. In some installations, cooler water from the circulating pumps is directed to the inputs of vertical jet pumps located between the core shroud and vessel wall (downcomer annulus) which provide a forced coolant circulation and effect a mixing of recirculating coolant with water returning from the steam separation and drying functions of the reactor vessel.

Proper inspection and maintenance of the coolant recirculating system is, of course, of high importance and certain of the procedures necessarily are involved due to radiation hazards. Inspection of the very large recirculation pumps typically requires removal of their large drive motors accompanied by a temporary storage thereof. Because of the size of the components, such storage typically is out of the reactor containment building itself. Following motor removal, to access the elongate drive shaft-impeller blade assembly of the pumps, the pump cover is unbolted and removed, whereupon a large radioactive shielding cask is positioned at the top of the pump and a grapple or hook then pulls the shaft into the cask. The cask and thus shielded drive shaft then are removed to another region of the reactor building whereupon some radiation contaminated depositions on the pump shaft are removed by a high pressure water jet system sometimes referred to as a "hydrolaser". Upon thus decontaminating the shaft, the now contaminated waste water from the cleaning procedure must be dealt with and the pump then is ready for inspection. Following inspection, for example employing any of a variety of non-destructive procedures, for example ultrasonic testing and the like, the drive shaft then can be reassembled within the pump structure and the motor is recoupled to the drive shaft. Typically this coupling takes place at a spacer coupling or connector link extending between the drive output of the motor and the driven input of the drive shaft of the pump. Such a link or coupling may have a length, for example, of about 12 inches as a minimum. The entire inspection procedure typically requires from several days to a matter of weeks to accomplish depending upon the difficulties encountered.

Similar inspection and maintenance problems also can occur in other reactor installation designs in which the moderator and working fluid are circulated independently, as in the pressurized water reactor (PWR). In a PWR, the primary loop that circulates water to the core is subject to radioactive conditions.

Inspection and maintenance of other pumps, as in chemical or petroleum facilities, often poses similar problems and hazards.

SUMMARY

The present invention is addressed to a method and apparatus for inspecting the shafts of recirculation pumps as are employed with nuclear reactor installations or chemical installations. An in situ technique of inspection is described which very substantially reduces the time span otherwise required to carry out shaft inspection. With the procedure, elongate inspection openings or bores are formed centrally within the recirculation pump shafts in the course of their original fabrication or upon their removal from the pump housings for the purposes of inspection in accordance with the prior stated elaborate procedures. Inspecting personnel access to the head or top of the normally vertically oriented inspection bores is achieved to a limited extent by the manual removal of a spacer coupling or link connecting the shaft of a large overhead electric motor with the top of the shaft of the recirculating pump. Such removal exposes an access region of limited vertical extent for the carrying out of non-destructive testing procedures utilizing the now exposed top of the inspection bore. Potential radiation exposure to inspecting personnel is controlled, inasmuch as the radioactive shaft remains within its radiation blocking water filled pump casing during the inspection procedure.

Ultrasonic testing is the preferred form of inspection and, for this purpose, a probe is provided having a diameter selected for slidable insertion with the inspection bore. This probe carries one or more ultrasonic transducers and is further dimensioned having a length limited for permitting its access to the inspection bore from the restricted access region. To support, and more importantly, maneuver the probe within the inspection bore or opening, a support assemblage accessible to the inspection bore through the access region is provided. However, it is necessary that the assembly maneuver the probe along a scanning locus to carry out inspection. This maneuver which is both vertical and rotational in extent is achievable in consequence of a recognition that the initial faults in pump shafts of the type now considered will initially occur only within certain regions of interest of highly limited vertical extent. Thus, the probe may be caused to traverse a scanning, raster type locus by actuation from the limited access region at the top of the pump shaft. Several days to weeks of inspection time are saved as a consequence of this novel procedure.

In one probe support assembly, a sequence of extension rods are assembled together in sequence at the limited access region as the probe is gradually lowered down the inspection bore or opening. Appropriate indicia are positioned with the procedure so as to monitor probe position and the like. By utilizing a mock-up of the shaft itself for the purpose of preliminary development of output recognition signals, certain characterizable regions of the pump such as labyrinth seals may be accurately located by the operator in the course of a subsequent inspection procedure. Thus, the region of interest where initial faults occur can be readily identified utilizing the readouts of ultrasonic inspection instrumentation. In another aspect of the invention, the maneuvering of the probe through its support assemblage can be carried out automatically and under computer control employing simple stepper motor technology. In the latter embodiment, even less potential exposure to radiation is present in the interest of inspection personnel safety.

Another feature of the invention provides a method for inspecting the shaft of a pump employed to circulate potentially hazardous fluid and removably connectable with a link of given length, in turn, connectable in driven relationship with a pump motor which comprises the steps of:

providing said shaft with an elongate inspection opening having a longitudinal axis and a predetermined cross-sectional dimension extending from the link connection to a predetermined region of interest;

removing said link to expose said inspection opening;

providing a probe supporting at least one ultrasonic transducer actuable to provide an inspection signal, the probe having a cross-sectional dimension less than said predetermined dimension, a length less than the given length and a connector portion;

providing a plurality of extension components, each having a cross-sectional dimension less than said predetermined dimension, a length less than the given length, and mutually oppositely disposed connector portions;

inserting the probe within the exposed inspection opening;

connecting the the connector portion of the probe with one said connector portion of a first extension component while the probe is within the inspection opening and inserting the first extension component within the inspection opening;

coupling a connector portion of a second extension component with another connector portion of first extension component while the first extension component is within the inspection opening and reiterating the interconnection and insertion within the inspection opening of the extension components to a last extension component when the probe is at the region of interest; and manipulating the probe along the region of interest while actuating the ultrasonic transducer to derive an inspection signal.

Another feature of the invention is the provision of a method for inspecting the shaft of a recirculation pump of a nuclear reactor installation, the pump having a motor removably coupled in driving relationship with a link of given length, in turn, coupled to one end of the shaft, the shaft being formed of given material having a longitudinal axis and extending to a characterizable portion and a shaft region of interest of given diameter, comprising the steps of:

providing the shaft having an elongate inspection bore of predetermined diameter extending substantially along the elongate axis from an access opening at the one end through the region of interest;

removing the link to expose the access opening and provide an access region of access length corresponding with the link given length;

providing a probe supporting at least one ultrasonic transducer actuable to provide an inspection signal, the probe having a diameter less than the bore predetermined diameter, a length less than the access length and a connector portion;

providing a probe support extension assembly connectable in supporting relationship with the probe for movably supporting said probe within the inspection base from the access region;

manipulating the extension assembly to move the probe through the inspection bore to the vicinity of the shaft characterizable portion;

actuating the ultrasonic transducer to derive the inspection signal locating a commencement of the region of interest with respect to the shaft characterizable portion;

manipulating the extension assembly to cause the probe to move defining a scanning pattern within the located region of interest; and actuating the ultrasonic transducer when the probe is within the scanning pattern to derive inspection signals.

Other objects of the invention will, in part, be obvious and will, in part, appear hereinafter.

The invention, accordingly, comprises the apparatus and method possessing the construction, combination of elements, arrangement of parts and steps which are exemplified in the following detailed disclosure. For a fuller understanding of the nature and objects of the invention, reference should be had to the following detailed description taken in connection with the accompanying drawings.

BRIEF DESCRIPTION OF THE DRAWINGS

FIG. 2 is a partial sectional view of a typical motor and pump assembly taken through the plane 2—2 in FIG. 1;

FIG. 3 is a sectional view of a pump shaft taken through the plane 3—3 in FIG. 2;

FIG. 4 is a fragmentary sectional view of a portion of a probe support assembly taken through the plane 4—4 in FIG. 3;

FIG. 7 is a front view of a mock-up assembly, with portions shown in phantom, employed for calibrating the apparatus of the invention;

DETAILED DESCRIPTION OF THE INVENTION

Figure 1:
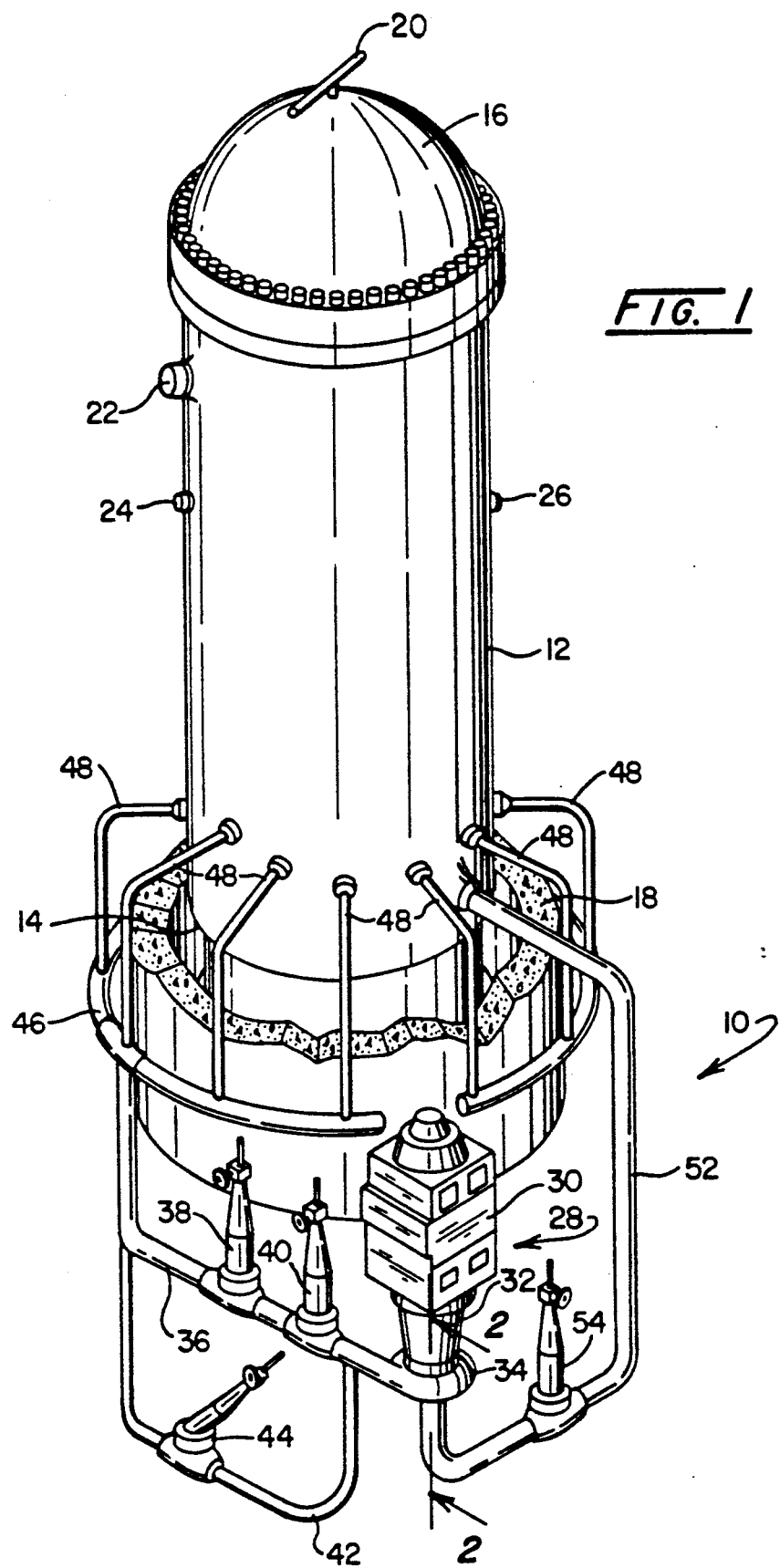
FIG. 1 is a simplified perspective view of a boiling water reactor and an associated water recirculation system.

Power installations employing nuclear reactor generated steam are relatively large and elaborate in scope. The reactor containment structure is of size sufficient to retain not only a reactor, which is several stories in height, but also associated cranes and related fuel handling structures, as well as certain pump and piping systems of the above-discussed water recirculation system. A portion of a latter recirculation system is shown in FIG. 1 in simplified pictorial fashion in order to provide context in which such a pump might operate. Looking to the figure, a water recirculation system is represented generally at 10 associated with a reactor 12 which extends from a vessel support skirt 14 to a hemispherical cap or head 16. Shown in broken away fashion as extending about the reactor 12 is a cylindrically shaped reactor shield wall 18 through which various implements extend for operative association with the reactor 12 including components of the recirculation system 10. These implements include a vent and head spray coupling 20, a steam outlet 22, a core spray inlet 24, and a feedwater inlet 26.

One of the two pumps of the recirculation system 10 is represented in general at 28 as including as electric motor 30, a generally vertically oriented pump body portion 32 which extends downwardly to a pump vane housing 34. The discharge line of pump 28 is shown at 36 extending from housing 34 and including discharge line shut-off valves 38 and 40. A bypass line is shown at 42 incorporating a bypass valve 44. Discharge line 36 is seen extending to a manifold 46 surrounding the assembly and from which a plurality of recirculation inlet lines 48 extend. Inlet lines 48 serve to feed jet pump assemblies (not shown) which are vertically oriented within reactor 12. A recirculation water outlet line 52 is shown extending from reactor 12 to the suction side of pump 28 and includes a recirculation loop suction valve 54.

Under the method of the present invention, the integrity of the shaft of pump 28 can be evaluated in situ with, in effect, a reduced potential for the occurrence of radiation exposure potentially harmful to facility personnel carrying out necessary preventive maintenance procedures. Obviated with this method are the requirements for removal of motor 30 utilizing the noted cranes and the like, as well as the necessary dismantling of pump housing 32 under radiation protective procedures. In this regard, reference is made to FIG. 2 in which a motor and pump assembly as at 28 again is represented. The pump body portion 32 is seen having a cylindrically shaped housing 60 attached to the motor 30 and into which the shaft of the motor 30 extends. a shaft collar assembly being connected therewith as represented at 62. Collar assembly 62, in turn, is removably connected by bolts or the like with a motor-pump spacer or link 64 which, in turn, is removably connected as by bolts to a corresponding collar 66 fixed to the shaft represented generally at 68 of the recirculating pump. The shaft 68 is seen to extend within a bearing seal assembly 70 which, in turn, extends to the lower pump housing 72 containing impeller components represented generally at 74. The suction input to the pump is represented at 76, while its discharge side is represented at 78. The entire assemblage 28 is positioned within the containment structure of a nuclear power facility. However, the spacer or link 64 is manually accessible through housing 60, conventionally by openings, for example, as represented at 81. The extent of this opening is limited and varies from installation to installation as does the size or length of the links 64. Generally, as a minimum, the link 64 will have a length of about 12 inches (30.5 cm).

Referring to FIG. 3, a representation of a shaft as typically may be found with pumps as at 28 is revealed in section. In the figure, the collar 66 again is portrayed but disconnected from the spacer or link 64. The shaft 68 is seen to extend from a top surface 80 at the top of collar 66, along an upper portion 82 of varying diameters until a labyrinth seal region 84 is encountered. The rectangular threads making up this labyrinth seal are configured for forming a pressure breakdown capability with corresponding complementary threads within the assembly 70. The labyrinth seal region 84 will be seen to serve as a characterizing portion of the shaft 68 for purposes of locating a region of interest 86 positioned just below it. This region of interest 86 extends to a journal represented generally at 88 and may be coupled to the shaft 68 by welding at side ring components thereof as at 90 and 92. Below the journal 88, the impeller 74 is located having appropriate impeller blades and the like.

In accordance with the procedure of the invention, an opening or inspection bore is formed within the shaft 68 concentrically with its longitudinal axis. This bore 100 is seen to extend from the shaft top surface 80 past the region of interest 86 and toward the bottom of journal 88 to terminate at 102. In general, shafts being inspected under the earlier lengthy techniques are provided with this bore 100 prior to their reinstallation within the pumps 28. Thus, future inspections may be carried out in situ in accordance with the teachings of the invention. In general, the inspection technique involves an accurate positioning of a probe as represented generally at 104 within the bore 100; the movement thereof along predetermined locus or pattern of movement; and the utilization of a nondestructive testing technique such as ultrasonic inspection employing transducers mounted with probe 104. Probe 104 is configured having a diameter less than that of the inspection bore 100 and a length which is selected for positioning it within the bore 100 from top surface 80 of shaft 68. The length of the probe 104, therefore, is less than the corresponding access length available upon the removal of spacer or link 64. To retain the probe 104 in position within the bore, as well as to maneuver it through a testing pattern or locus of test orientations, it is supported by an assemblage of discrete extension components as represented at 106a–106e. The extension components 106a–106e are of similar dimension to probe 104 in that their length is less than the accessible length available with the removal of link or spacer 64 and their diameter is less than the corresponding diameter of inspection bore 100. As a preliminary assembly, the components 106a–106e are associated only by internal cabling 108 which, inter alia, serves to provide control inputs and to convey sampling signal data. However, when sequentially positioned within the inspection bore 100, the probe 104 and associated extension components are interconnected. In this regard, the initial extension component such as that at 106a may threadably engage one end of probe 104. Extension component 106a and the succeeding such components then may be interconnected by a series of interposed short threaded collars as at 110a–110d. Collar 110d is seen to be located for attachment with the upwardly disposed end of extension component 106d. This interconnection of extension components, for example the association of components 106c and 106d with collar 110c is revealed in FIG. 4.

The preferred non-destructive examination technique employed with the probe 104 is that of ultrasonic testing. This volumetric inspection method provides for the examination of materials through the transmission of high frequency sound waves. Generally, the frequencies elected are between 200 KHz and 16 MHz. Four basic categories and procedures for ultrasonic testing, characterized by the variable being measured are generally identified. Those categories are the resonant frequency method; the intensity methods; transit time methods; and intensity in transit time methods (ITT). The most comprehensive and widely used of those methods are the intensity and transmit time methods which are employed to locate or differentiate flaws. Of this latter, more popular (ITT) approach, two methods occur, to wit, a pulse transit time method (pulse echo) and a frequency method. The pulse-echo approach employs short pulses of ultrasound working essentially in the same manner as sonar. In this regard, a transducer is employed to generate a pulse of ultra sound which is reflected back to a receiver by either a discontinuity or a back or reflecting wall. The size of the peak of the return echo is proportional to the echo's amplitude and contains information about the size of the reflecting surface or flaw. The depth or position of the flaw or the like can also be determined from this reflected sampling information. In general, ultrasonic test equipment will include a power supply; a pulse generator; a receiver-amplifier; a clock; an oscilloscope for readout purposes, and any of a variety of transducers which function to send or receive sampling signals or to carry on both functions. Typically, these devices are implemented by piezoelectric based structures.

The equipment employed with the data to follow utilize the pulse-echo method and, in particular, a C-scan approach. With this approach, the transducer or in the instant employment, a probe carrying a transducer is maneuvered across a region of interest, the typical pattern or locus of movement being a sequence of parallel lines not unlike a raster. The C-scan implemented equipment further employs a "depth gate". This implementation allows only discontinuity signals from between two selected depths to be displayed. Thus, the operator is permitted to reject the front surface and backwall echoes which otherwise might obscure flaws.

Figure 5:
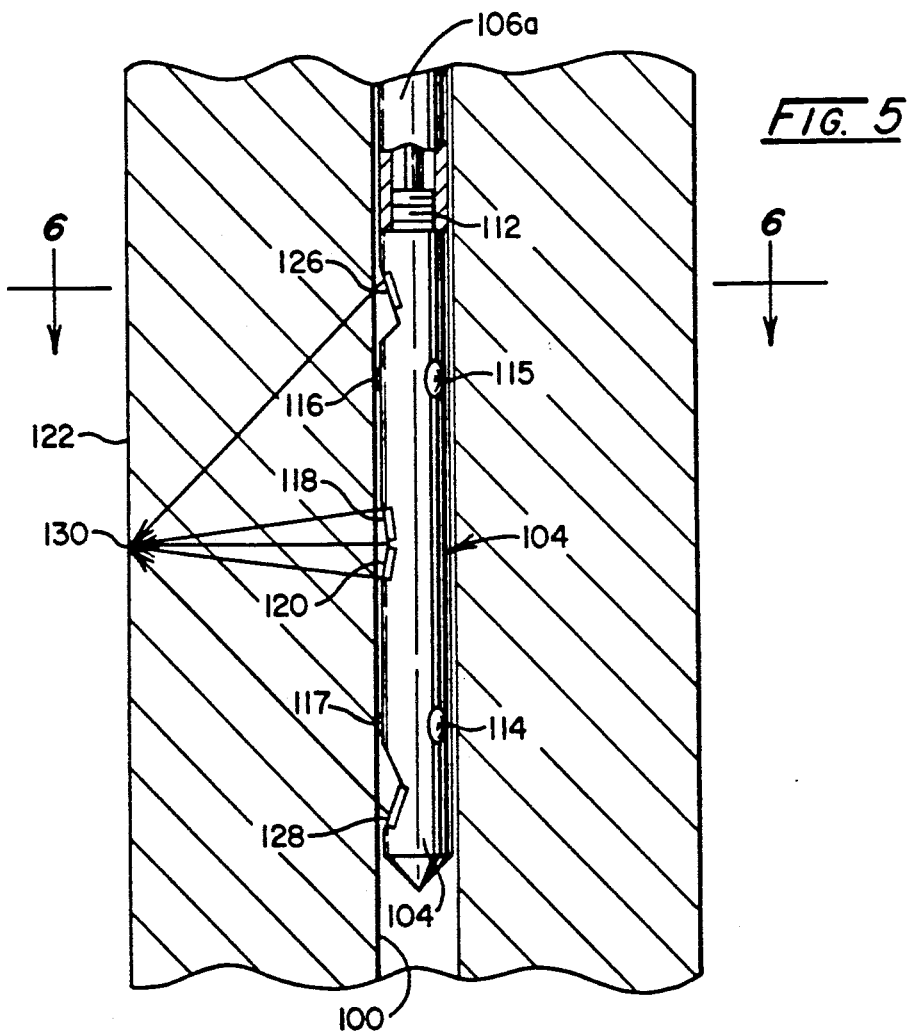
FIG. 5 is a partial sectional view of a probe formed according to the invention taken through the plane 5—5 in FIG. 3.

Now looking to the configuration of probe 104 as it is employed for ultrasonic examination, reference is made to FIG. 5 wherein the probe 104 is seen positioned within inspection opening 100 and attached by threaded connection 112 with extension component 106a. Probe 104 is slidably oriented within the inspection bore 100 by four outwardly biased spacers 114–117. Mounted substantially centrally of the probe 104 are dual element pitch-catch 5 MHz ½ inch diameter devices 118 and 120. Devices 118 and 120 are inclined such that the beam generated thereby is focused at the outside surface represented at 122 of the region of interest 86. With the pitch-catch arrangement, one transducer such as that at 118 is designated for transmission while the other such as that at 120 is designated for reception. With such devices, different materials may be employed to closely match the function of each transducer. Looking additionally to FIG. 6, the dual send/receive straight beam is graphically depicted.

Figure 6:
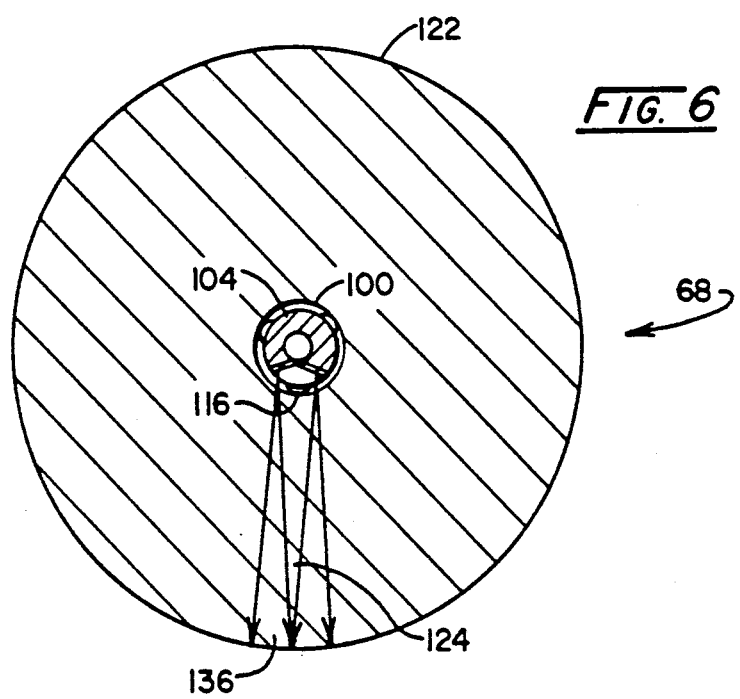
FIG. 6 is a sectional view taken through the plane 6—6 in FIG. 5 and showing ultrasonic transducer beam regions.

Additionally positioned upon the probe 104 are two, 2.25 MHz, ½ inch diameter 45° shear wave transducers 126 and 128. Transducer 126 is oriented downwardly, while, conversely, transducer 128 is oriented upwardly. The two transducers 126 and 128 are spaced apart a distance corresponding with the diameter of the shaft at the region of interest and thus converge at a single location represented at 130. The upward and downward looking 45° shear waves as evolved from transducers 126 and 128 are represented in FIG. 6 at 136.

To carry out ultrasonic testing employing probe 104 with any given shaft such as that at 68, as preliminary procedure, it is necessary to prepare a mock-up of the shaft employing acoustically equivalent material or the same material which is employed in fabricating the shaft itself, for example stainless steel. The mock-up is prepared having a profile mimicking certain of the desired characterizable features of the shaft, as well as the region of interest 86. In this regard, by employing the labyrinth region 84 as a characterizable region, data may be developed for locating the region of interest 86. Similarly, the lower extent of region 86 may be further identified by locating features such a the journal components 88. The region of interest 86 is so designated because it has been determined that the initial faults which will develop in a shaft as at 68 will be surface located circumferentially oriented crack type faults at region 86. Thus, identification and differentiation of such faults at that location will represent a first fault condition to be experienced by shaft 68. It further may be observed that the region 86 is of considerably limited extent with respect to the overall size of the shaft 68. Thus, a scanning technique which is of practical extent with respect to the limited space available at the removed link 64 region becomes achievable.

Figure 8:
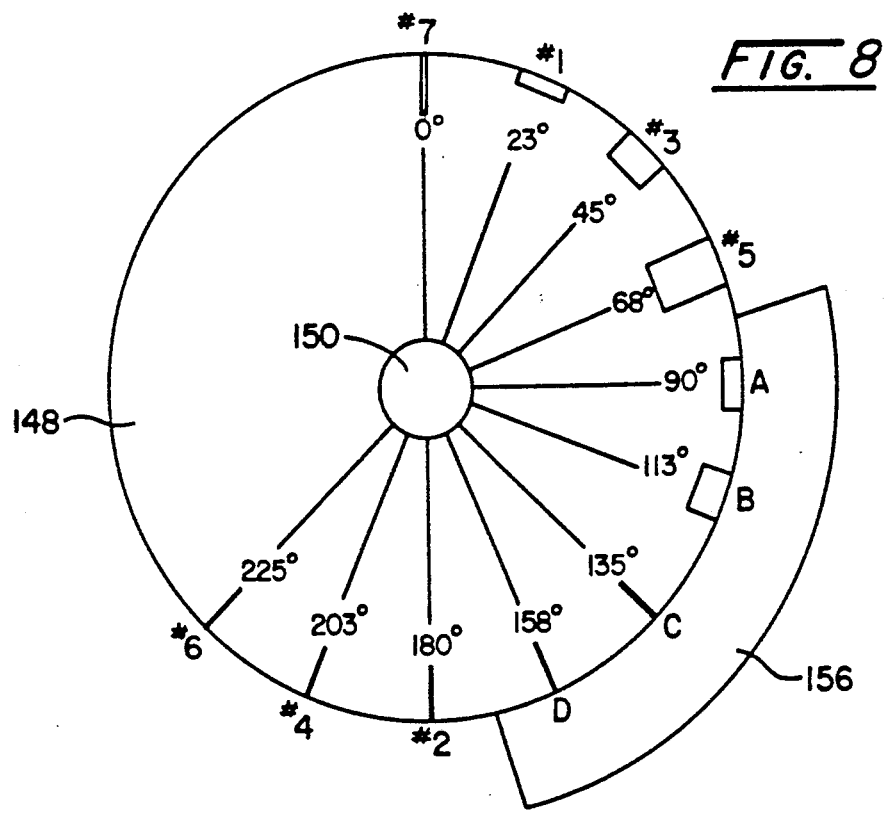
FIG. 8 is a top view of portions of the apparatus of FIG. 7 showing the azimuth location of reflector notches and bores.

Looking to FIG. 7, a mock-up suited, for example for use with the exemplary shaft 68 is revealed generally at 140. The mock-up 140 includes an insertion tube portion 142 having an interior bore 144 corresponding with the inspection bore 100. Tube 142 is welded at 146 to a shaft emulator cylinder 148 through which the bore as at 144 is continued as represented in phantom. The cylinder 148 is configured having the same diameter as the region of interest 86 of shaft 68 and the upward portion thereof at 152 is machined in a manner duplicating the labyrinth seal 84 of shaft 68. Spaced below the labyrinth seal mimicking portion 152 is a region 154 which generally will correspond with the region of interest 86 of shaft 68. Accordingly, just below region 154 is an arcuate journal side ring simulator 156 which is fillet welded to the cylinder 148 on both sides and along its entire length. A sequence of reflector slots are machined into the surface of lock-up 140 at the locations identified as numbers 1 through 6 and a through d, the latter being beneath the journal side ring simulator 156. Reflector number 7 is a ¼ inch diameter side drilled hole employed in particular in alignment procedures associated with pitch-catch transducers 118-120. The azimuth orientations of these reflector positions are represented in FIG. 8 of the drawings. Note that reflectors 1, 3, 5, A, and B are oriented in a circumferential sense with respect to the longitudinal axis of device 140, while reflectors 2, 4, 6, C, and D are oriented in parallel with that axis.

The defect parameters established by the above notches, bores, or suitable reflectors for device 104 are provided in the tabulation which follows below.

| DEFECT PARAMETERS | | | | | |
|---|---|---|---|---|---|
| Notch | 1 | 3 | 5 | 2 | 4 | 6 |
| Length | ¼" | ¼" | ¼" | 1" | 1" | 1" |
| Depth | 0.100" | 0.300" | 0.700" | 0.100" | 0.300" | 0.700" |
| Notch | A | B | C | D | 7 |
| Length | ¼" | ¼" | ¼" | ¼" | ¼" |
| Depth | 0.200" | 0.500" | 0.200" | 0.500" | ¼" |

Figure 9:
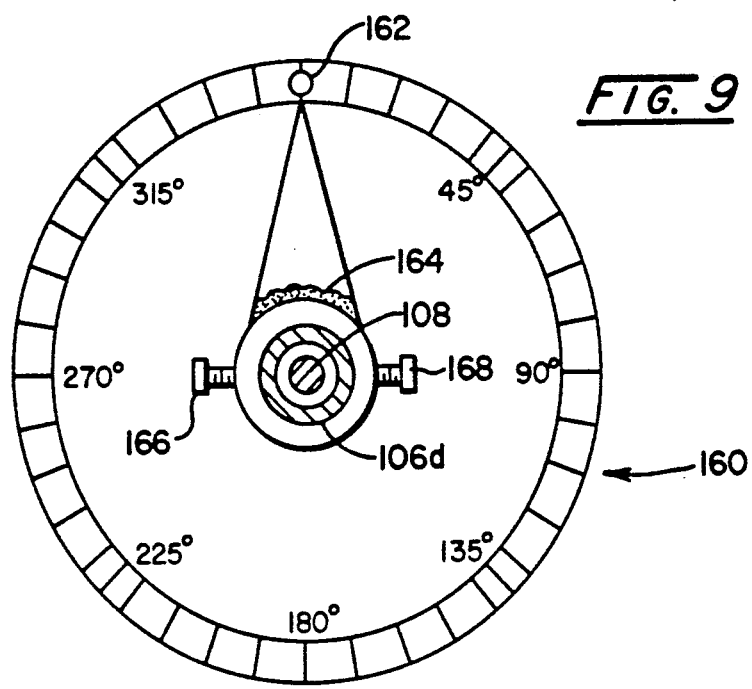
FIG. 9 is a top view of an azimuth degree indicator and pointer as assembled with an extension component and cabling devices of the apparatus of the invention.

In carrying out a calibration procedure with the device 140, it is necessary to develop a determination of the angular orientation of the probe 104 as well as its vertical orientation. The calbration typically is manual and, for this purpose, an azimuth or degree indicator plate such as that revealed at 160 in FIG. 9 is employed. The plate 160 also may be utilized in carrying out a manual form of examination of an in situ pump as revealed by its presence at the upper surface 80 in FIG. 3. The plate 160 is seen having degree indicia extending around it from 0° to 360°. At the 0°-360° location, a ¼ inch bore at 162 is provided for purposes of alignment, particularly with respect to its use for manual inspection in the manner shown in FIG. 3. To provide for shaft position reference, a degree pointer 164 is provided having a collar which fits over a first extension component as at 106a (FIG. 5) and is retained in place by thumb screws as at 166.

In carrying out a calibration procedure, for example on a simpler manual basis, certain of the reflection points shown in FIG. 7 are of a higher level of importance than the others. In this regard, notches having a horizontal orientation are of particular interest because this is the orientation of the first faults which will be developed at the region of interest in the pump shaft. Inasmuch as manual utilization of the system typically calls for the use of equipment which is portable in nature, for example a detector identified as "EPOCH 2002" marketed by Panametrics, Inc., Waltham, Mass., the calibration procedure may be limited to operation of one transducer at a time. In the manual calibration procedure, which is closely similar to an automated approach, the mock-up device 140 is positioned vertically and the inspection bore 132 is filled with a couplant such as demineralized water. The probe is assembled with an appropriate number of extension components such as that at 106a and the appropriate transducers are mounted thereon. The azimuth indicator plate 160 is attached to device 140 and pointer 164 is positioned thereover at a location permitting vertical movement of the system within the limited region of interest. Generally, the pointer is aligned with the focus of straight beam trandsucers 118 and 120. The probe 104 then is lowered within bore 142 until a return reflection from the simulative labyrinth seal 152 is observed on the display of the ultrasonic testing instrument. This is a characterizable region. Probe 104 then is lowered until the straight beam transducers 118-120 response is reflecting from the smooth region 154 of device 148 just below the labyrinth thread region 152. At this position, instrument adjustments are made to display for back reflection from the outside surface and adjustments are made to the sweep and delay controls to accurately position these reflectors at predetermined locations on the instruments baseline sweep.

The probe 104 is then positioned such that the straight beam transducer combination 118 and 120 detects the ¼ inch side drilled hole or reflector number 7 (FIG. 7) at a maximized return signal. The amplitude of the instrument then is set at between 90% and 100% of full screen height. Additionally, the number of of degrees between the 50% of screen amplitude points as probe 104 is rotated across this reflector number 7 may be noted and recorded.

The downwardly looking pulse echo transducer 126 then may be calibrated. In this regard, the probe 104 may be positioned to locate defect or reflector number 1 and its return signal is maximized, screen height being adjusted to between 95% and 100% of full screen height. Next, a determination and recordation is made of the number of 5° scan indexes required for this shear wave to pass across notch number 1 which is ¼ inch in length. The procedure is then repeated for upwardly looking transducer 128.

The remaining notches may then be located and the readouts evaluated at the option of the operator.

FIGS. 10A through 10D are representations of the screen readouts developed through the utilization of a probe as at 104 with a mock-up device as at 140. The instrumentation utilized was the above-noted equipment by Panametrics, Inc. Looking to FIG. 10A, an identification of notch number 1 shown in FIG. 7 having a depth of 0.100 inch, the shallowest notch is revealed within the readout gate profile 180 at 182. This readout was developed from the lower transducer 128 having an upwardly directed 45° cant. The instrumentation additionally will display identification of the horizontal distance to the notch (not shown).

Figure 10A:
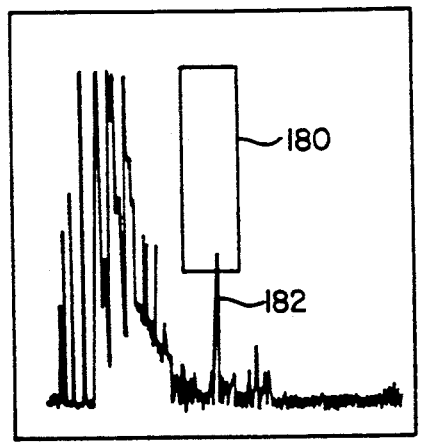
FIGS. 10A-10D show ultrasonic instrumentation readouts corresponding with the performance of a probe according to the invention utilized with the mock-up apparatus of FIG. 7.
Figure 10B:
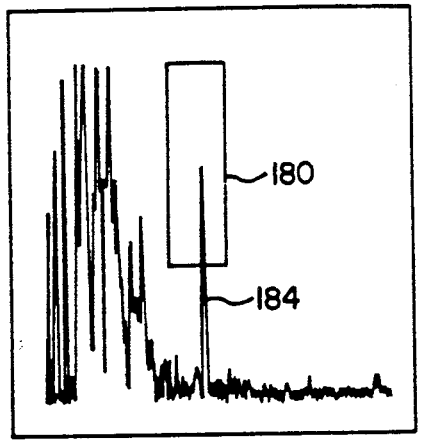

In FIG. 10B, a signal 184 represents a readout of notch or reflector number 3 as developed from transducer 128. This notch is deeper, having a depth of 0.300 inch and it may be observed that the amplitude of the readout is higher.

Figure 10C:
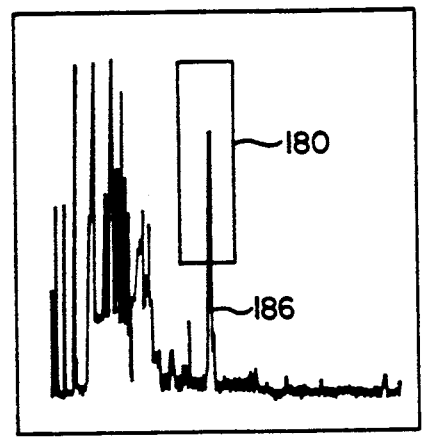

Looking to FIG. 10C, a readout from transducer 128 looking to notch or reflector number 5 is shown at 186 within gate 180. Notch number 5 is the deepest of the notches having a depth of 0.700 inch. The amplitude of signal 186 may be observed to be higher.

Figure 10D:
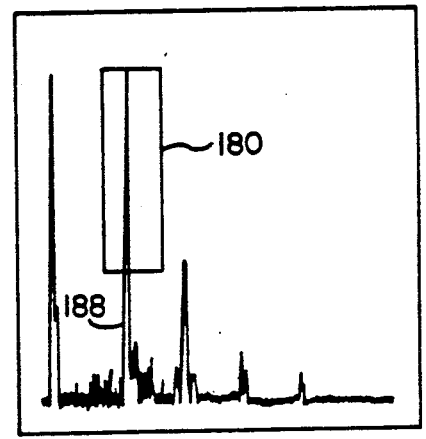

FIG. 10D reveals a signal 188 representing a readout of transducer pair 118-120 with respect to the smooth surface of device 140. The thickness information provided with the readout (not shown) was found to correspond with that developed, for example, in conjunction with FIG. 10C.

The manual procedure for carrying out a nondestructive testing of a shaft as represented at 68 in FIG. 3 involves the initial steps as described above of calibrating the instrumentation. Following such calibration, the azimuth or degree indicator earlier described at 160 may be positioned at the top surface of the shaft and the 0° location thereof 162 aligned with a corresponding designated 0° position on the shaft. A pin or the like extending into a small bore in shaft 68 may be utilized to secure the device 160 in an appropriate orientation. The opening within the degree indicator is aligned with inspection bore 100. The shaft 68 will have a normal vertical orientation and the inspection bore 100 is filled with a suitable couplant such as demineralized water. This couplant is the same couplant which is utilized in the earlier-described calibration procedures. Employing the pitch-catch transducer combination 118–120, the probe is then lowered within the inspection bore 100 until the labyrinth seal grooves at region 84 are identified as the probe 104 moves across that region. A broad based signal will be observed at the output screen of the instrumentation which is caused by the constant changing cross section of the groove architecture. Preferably, a number of the last remaining of such groups is identified leading to where the smooth region of interest 86 commences. As the probe 104 passes the last of such grooves and region 86 is encountered, a smooth cross-section sampling signal may be observed. This smooth section constitutes the region of interest following the earlier-described characterization zone identifying the region of interest. It is desirable to mark the beginning and end points of these zones on the shaft upper portion above top surface 80. The top fillet weld which attaches the top side ring 90 of the journal 88 to the pump shaft is seen next. The probe shaft should be marked accordingly at this position. The next signal seen will be the bottom weld attaching that ring 90 to the pump shaft which may be considered a next zone of characterization. Further zones of characterization may be developed as the probe 104 is moved further down the shaft. However, it is the region of interest 86 which is of paramount interest in the procedure. Appropriate recordations are made of the vertical positioning of these characterization zones and regions of interest. This information provides the examining personnel with information as to the length of stroke required for the inspection zones desired. This information normally is compared with corresponding dimensions on the drawings of the shaft itself.

Following the above preliminary procedures, the degree pointer 164 may be attached to the extension component extending through the plate 160 and top surface 80 of the shaft. Preferably, this device is located so as to serve as a limit or stop defining the extent of downward travel for the first of the inspection zones to be evaluated.

Figure 11A:
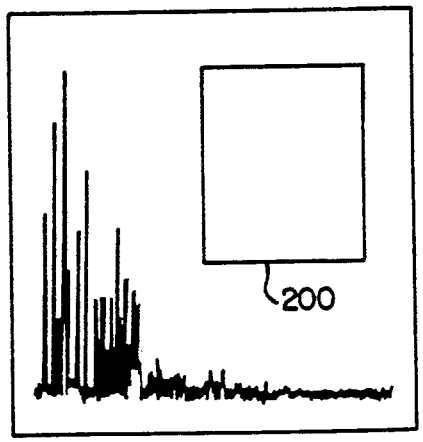
FIGS. 11A-11M are ultrasonic testing instrumentation readouts for operation of a probe according to the method of the invention with a boiling water reactor recirculating pump shaft.

Referring to FIG. 11A, the instrument screen readout is presented representing the sampling signals or axial shear wave looking downward as developed from transducer 126. The screen is gated as represented at boundary or readout gate profile 200. FIG. 11A is a typical screen presentation as the probe 104 is moved within a smooth (no fault) surface portion of the shaft 68. The high level signals to the left of the gate 200 represent sound energy reflecting from around the inside surfaces of bore 100.

Figure 11B:
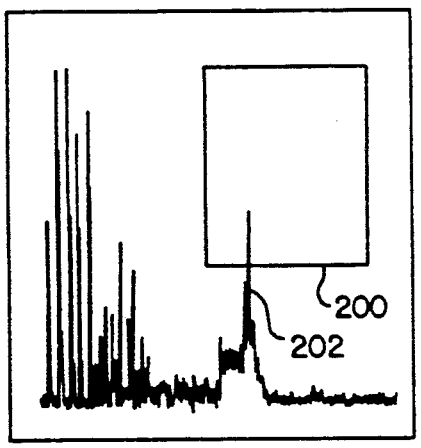

Looking to FIG. 11B, the gate profile 200 again is revealed, the signals to the left of gate 200 again representing reflections from the inner bore 100. The signals 202 to the right or below the gate profile 200 are typical signals reflecting from the threads of the labyrinth seal region 84 as the probe 104 is moved along that region. The signals, as before, are generated from downward looking transducer 126.

Figure 11C:
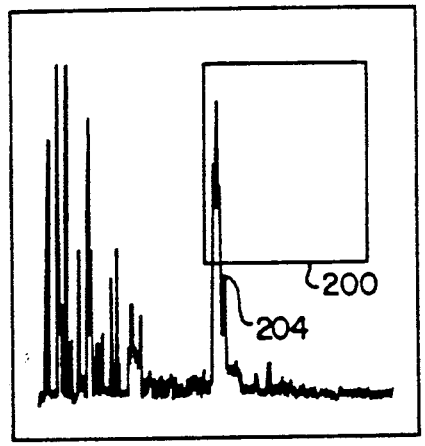

FIG. 11C shows the response from transducer 126 providing a shear wave looking downwardly, the high level signal 204 emanating from the upper journal to shaft weld, i.e. at side ring 90. This shaft weld creates almost a right angle reflection to the transducer 126 and thus a high amplitude is recognized. In effect, the operator knows that the transducer 126 is looking below the region of interest 86 with the presence of this signal. Thus, the signal represents an area of characterization showing the end of region 86.

Figure 11D:
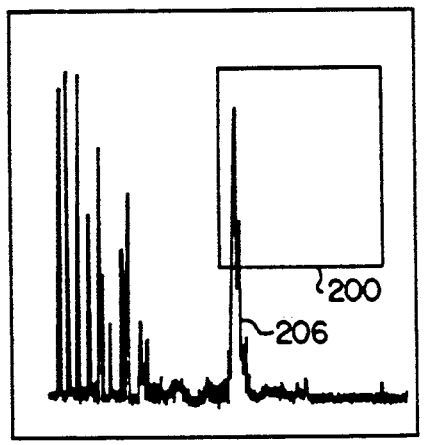

FIG. 11D shows the gate 200 in conjunction with a signal 206 generated from downlooking transducer 126 as it responds to signals from the lower shaft-to-journal weld or lower side ring weld 92. Again, the signal 206 representing this weld is of relatively higher magnitude. Note that signal 206 bears a resemblance to signal 204, both representing a fillet weld.

Figure 11E:
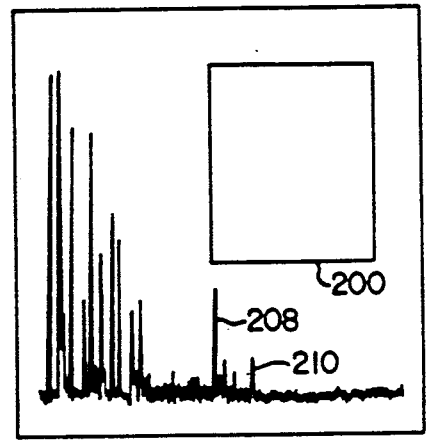
Figure 11F:
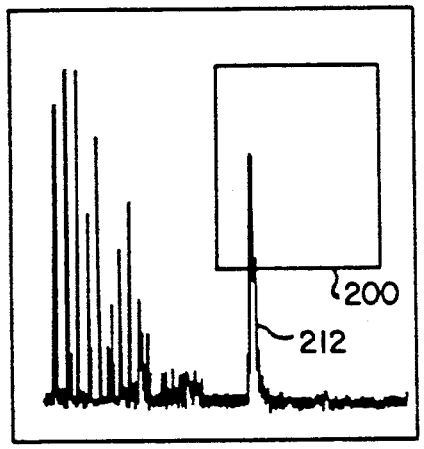

FIG. 11E again shows a response of instrumentation to the activity of transducer 126 as its beam is moved below the upper journal-to-shaft weld. The signal representing the weld now is decreasing as represented at 210. However a next signal 208 is commencing to be recognized. This signal is representative of a circumferential groove within the shaft at this location. As the probe 104 is moved further downwardly, the groove representative signal is seen to increase in amplitude as represented in FIG. 11F at 212. The gate periphery again is shown at 200.

Figure 11G:
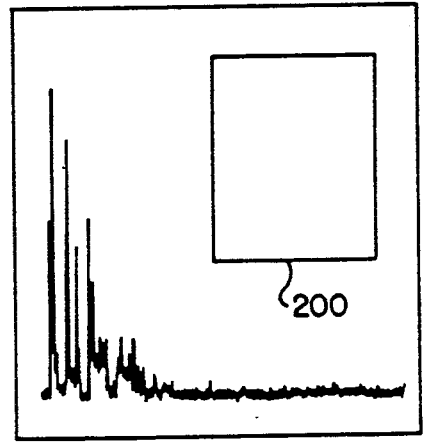

FIG. 11G is a representation of the screen readout with the gate 200 profile being shown. The signal developed for this figure was from upward looking transducer 128 as the probe 104 was positioned at the bottom of shaft 100. This display is typical for signals looking to regions of the shaft surface having no cross-sectional changes as may otherwise be evidenced by welds, journal fittings, labyrinth seals and the like.

Figure 11H:
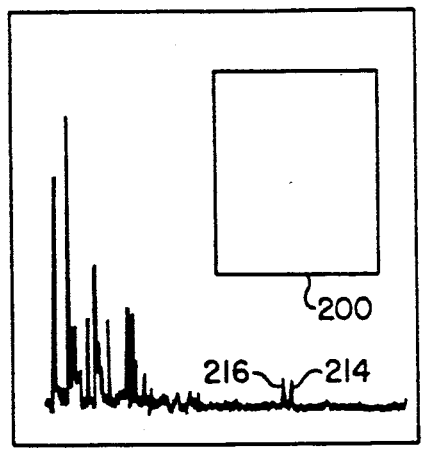
Figure 11I:
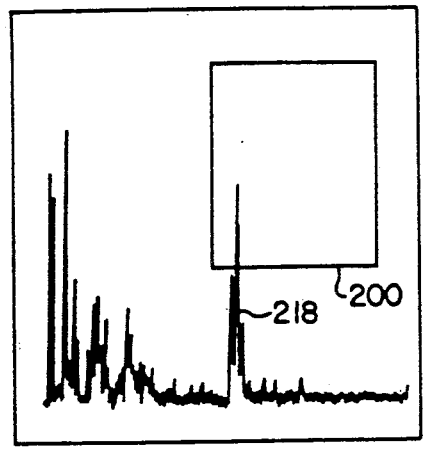
Figure 11J:
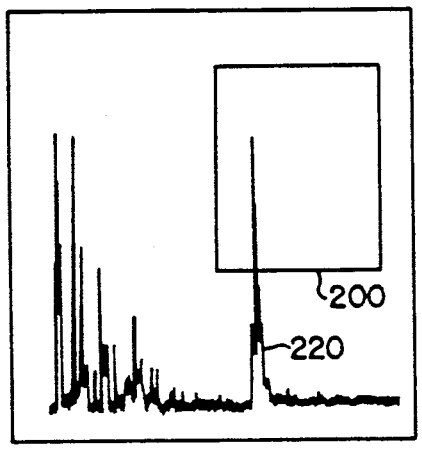
Figure 11K:
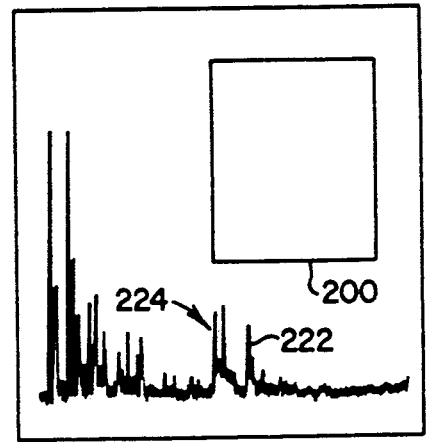
Figure 11L:
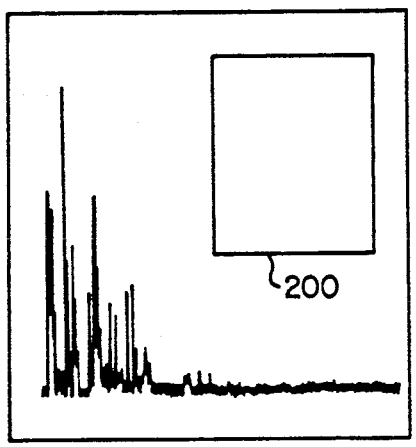

FIG. 11H shows the display response from transducer 128 as the probe 104 commences to be elevated from the bottom of the shaft 100. While the signals to the left of the figure represent the surface of bore 100, the small signals 214 and 216 to the right thereof represent the upper journal to shaft weld, i.e. a weld at side ring 90, as it commences to be detected. As the probe 104 is scanned upwardly within inspection bore 100, the signals increase as represented in FIG. 11I wherein the upper journal to shaft weld now has the amplitude as represented at 218. FIG. 11J shows the progress of signal 218 to have maximized as represented at 220. As probe 104 continues to be elevated, the signals from transducer 126 representing the upper journal to shaft fillet weld at ring 90 diminish as represented at signal 222, while the signals representing the teeth of the labyrinth seal at region 84 commence to develop as represented at 224. As probe 104 continues to be elevated above the labyringth seal area 84, a smooth surface component of shaft 78 is developed and the resultant signal representing such smooth surface is shown in FIG. 11L.

Figure 11M:
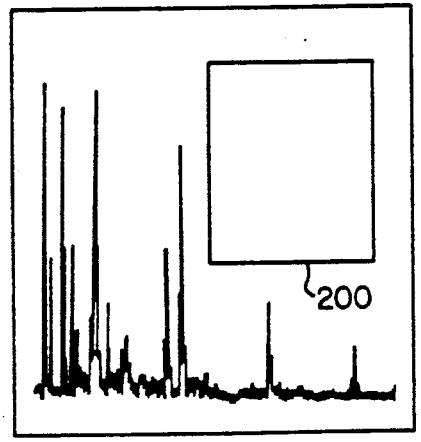

FIG. 11M shows a typical output display generated by the transducer pair 118 and 120 at higher elevations in shaft 68, the display showing multiple wall thicknesses. In the representations above in connection with FIGS. 11A–11L, the examination resulted in an affirmative determination that no faults existed within the shaft.

Figure 12:
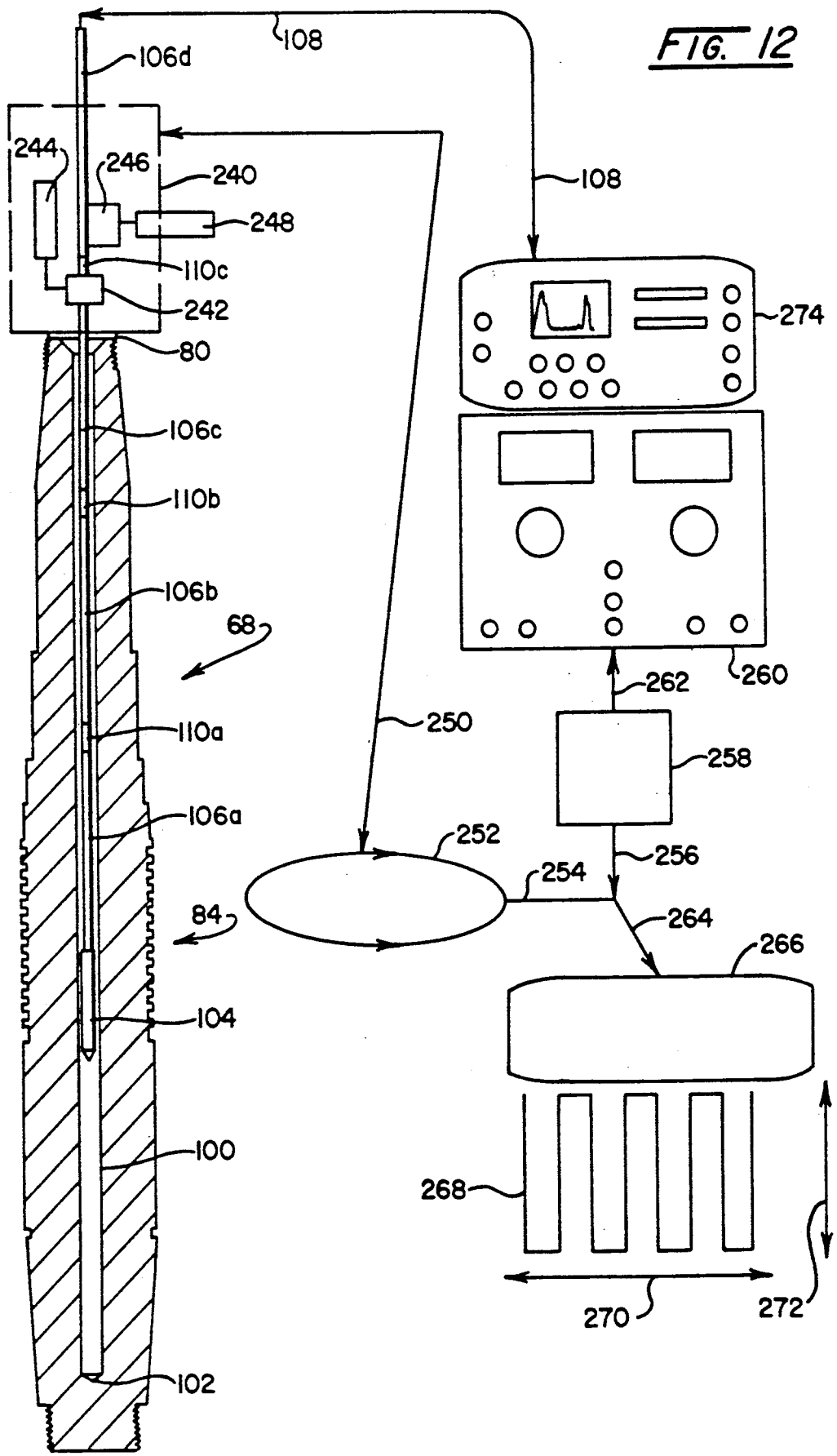
FIG. 12 is a schematic portrayal of a motorized implementation of the method of the invention.

Because very low forces are required to maneuver the probe 104 and its associated supporting components within the inspection bore or opening 100, the inspection technique is readily suited to a more mechanized examination procedure. Such procedures also prove advantageous in further lessening the opportunity of exposure for inspecting personnel to radiation. In FIG. 12, a mechanized version of the inspection procedure is represented in schematic form. In the figure, a shaft such as that described at 68 is reproduced with the same identifying numeration, however, the collar component of it 66 is not shown. Above the shaft a simple drive mechanism represented in dashed boundary 240 is positioned over the upper surface 80 of shaft 68. This mechanism includes a rotational engaging component 242 which provides an indexed movement of the assemblage of probe 104 and the extension components 106 about the central axis of the bore 100 and probe 104. A stepper form of motor drive input to device 242 is represented at 244. While imparting rotational movement to the assemblage of probe 104 and extension components 106, the device 242 also permits slidable vertical movement. In the latter regard, vertical movement is imparted in an indexing fashion to the assemblage of probe 104 and extension components 106 as represented by vertical engaging component 246 operating in vertical indexing fashion with respect to the assemblage by virtue of drive imparted from a stepper motor 248. Control over motors 244 and 248 is depicted by lines 250 and 252 which are seen coupled via lines 254 and 256 to a driver output stage 258 which, in turn, is controlled from a programmable motor controller 260 as represented at line 262. The raster scan form of rotational and vertical movement is schematically depicted in the drawing by arrow 264, block 266, and developed locus of motion path 268. The circumferential extent of this locus 268 is represented by the extent of arrow 270 while, correspondingly, the vertical scan height or locus of movement is represented at arrow 272. During the scanning operations, output cabling 108 is seen directed to a multichannel ultrasonic and data instrument acquisition system represented at 274. Device 274 may be provided, for example, as a computer controlled ultrasonic testing instrument sold under the trade designation "TOMASCAN" by Tecrad Corporation of East Lyme, Conn.

Since certain changes may be made in the above described method and apparatus without departing from the scope of the invention herein involved, it is intended that all matter contained in the description thereof or shown in the accompanying drawings shall be interpreted as illustrative and not in a limiting sense.

We claim:

1. Method for inspecting a shaft of a pump employed to circulate potentially hazardous fluid and removably connectable with a link of given length, in turn, connectable in driven relationship with a pump motor comprising the steps of:

providing said shaft with an elongate inspection opening having a longitudinal axis and a predetermined cross-sectional dimension extending from said link connection to a predetermined region of interest;

removing said link to expose said inspection opening;

providing a probe supporting at least one ultrasonic transducer actuable to provide an inspection signal, said probe having a cross-sectional dimension less than said predetermined dimension, a length less than said given length and a connector portion;

providing a plurality of extension components, each having a cross-sectional dimension less than said predetermined dimension, a length less than said given length, and mutually oppositely disposed connector portions;

inserting said probe within said exposed inspection opening;

connecting the said connector portion of said probe with one said connector portion of a first said extension component while said probe is within said inspection opening and inserting said first extension component within said inspection opening;

coupling a said connector portion of a second said extension component with another connector portion of said first extension component while said first extension component is within said inspection opening and reiterating the interconnection and insertion within said inspection opening of said extension components to a last said extension component when said probe is at said region of interest; and manipulating said probe along said region of interest while actuating said ultrasonic transducer to derive said inspection signal.

2. The method of claim 1 in which said step of manipulating said probe is carried out by rotation about and movement along said longitudinal axis.

3. The method of claim 2 in which said rotation and movement are carried out by applying corresponding forces to said last extension component.

4. The method of claim 3 including the steps of:

providing a motor driven rotational control connectable with said last extension component for drivably, indexably rotating said probe about said longitudinal axis to a sequence of scan azimuth positions; and providing a motor driven longitudinal control connectable with said last extension component for drivably, reciprocally moving said probe along said longitudinal axis within said region of interest at said scan azimuth positions.

5. The method of claim 3 in which said rotation and movement are carried out by indexably rotating said probe about said longitudinal axis to a predetermined sequence of scan azimuth positions, and reciprocally moving said probe along said longitudinal axis an extent effective for scanning within said region of interest at said scan azimuth positions.

6. The method of claim 1 in which said probe is provided having first and second ultrasonic shear wave transducers mutually spaced and angularly oriented to access a common point at the surface of said shaft at said region of interest.

7. The method of claim 6 in which said first and second transducers are mutually inwardly angularly oriented at about 45° with respect to said longitudinal axis and are mutually spaced therealong a distance corresponding with the diameter of said shaft at said region of interest.

8. The method of claim 6 in which said probe is provided having a dual element, pitch/catch ultrasonic transducer pair configured to effect a focus of the beam generated thereby at said common point.

9. The method of claim 1 in which said probe is provided having a dual element, pitch/catch ultrasonic transducer pair configured with respect to said longitudinal axis to effect a focus of a beam generated thereby at a point at the surface of said shaft at said region of interest.

10. A method for inspecting the shaft of a recirculation pump of a nuclear reactor installation, said pump having a motor removably coupled in driving relationship with a link of given length, in turn, coupled to one end of said shaft, said shaft being formed of given material having a longitudinal axis and extending to a characterizable portion and a shaft region of interest of given diameter, comprising the steps of:

provided a said shaft having an elongate inspection bore of predetermined diameter extending substantially along said elongate axis from an access opening at said one end through said region of interest;

removing said link to expose said access opening and provide an access region of access length corresponding with said link given length;

providing a probe supporting at least one ultrasonic transducer actuable to provide an inspection signal, said probe having a diameter less than said bore predetermined diameter, a length less than said access length and a connector portion;

providing a probe support extension assembly connectable in supporting relationship with said probe for movably supporting said probe within said inspection bore from said access region;

manipulating said extension assembly to move said probe through said inspection bore to the vicinity of said shaft characterizable portion;

actuating said ultrasonic transducer to derive said inspection signal locating a commencement of said region of interest with respect to said shaft characterizable portion;

manipulating said extension assembly to cause said probe to move defining a scanning pattern within said located region of interest; and actuating said ultrasonic transducer when said probe is within said scanning pattern to derive inspection signals.

11. The method of claim 10 in which said shaft characterizable portion is a labyrinth seal and said region of interest extends a predetermined distance therefrom along said longitudinal axis.

12. The method of claim 10 including the steps of:

providing a calibrating mock-up of said shaft characterizable portion and region of interest, said mock-up being formed of said given material, having a portion simulative of said shaft characterizable portion, and said region of interest and having a simulative bore extending therethrough of said predetermined diameter corresponding with said inspection bore; and inserting said probe within said simulative base and actuating said simulative transducer to derive simulative inspection signals characterizing said commencement of said region of interest for employment to locate said region of interest of said shaft.

13. The method of claim 12 in which said shaft characterizable portion is a labyrinth seal and said region of interest extends a predetermined distance therefrom along said longitudinal axis.

14. The method of claim 10 in which said probe is provided having first and second ultrasonic shear wave transducers mutually spaced and angularly oriented to access a common point at the surface of said shaft at said region of interest.

15. The method of claim 14 in which said first and second transducers are mutually inwardly angularly oriented at about 45° with respect to said longitudinal axis and are mutually spaced therealong a distance corresponding with the diameter of said shaft at said region of interest.

16. The method of claim 10 in which said probe is provided having a dual element, pitch/catch ultrasonic transducer pair configured with respect to said longitudinal axis to effect a focus of a beam generated thereby at a point at the surface of said shaft at said region of interest.

* * * * *